United States Patent
Antaki et al.

(10) Patent No.: US 7,338,521 B2
(45) Date of Patent: Mar. 4, 2008

(54) LOW PROFILE INLET FOR AN IMPLANTABLE BLOOD PUMP

(75) Inventors: James F. Antaki, Pittsburgh, PA (US); Jed C. Ludlow, North Salt Lake, UT (US); Scott D. Miles, Sandy, UT (US)

(73) Assignee: World Heart, Inc., Oakland, CA (US)

( * ) Notice: Subject to any disclaimer, the term of this patent is extended or adjusted under 35 U.S.C. 154(b) by 0 days.

(21) Appl. No.: 10/171,458

(22) Filed: Jun. 13, 2002

(65) Prior Publication Data
US 2003/0233144 A1 Dec. 18, 2003

(51) Int. Cl.
*A61M 1/10* (2006.01)
(52) U.S. Cl. .............. 623/3.26; 415/208.1; 417/423.7; 604/6.11; 600/16
(58) Field of Classification Search .............. 623/3.26; 415/208.1, 900; 417/423.7; 604/6.11; 600/16
See application file for complete search history.

(56) References Cited

U.S. PATENT DOCUMENTS

| | | | |
|---|---|---|---|
| 3,311,292 A * | 3/1967 | Connor ..................... | 415/211.2 |
| 3,735,782 A * | 5/1973 | Strscheletzky ............... | 138/39 |
| 3,860,300 A | 1/1975 | Lyman ......................... | 308/10 |
| 4,037,984 A * | 7/1977 | Rafferty et al. ............... | 415/60 |
| 4,683,391 A | 7/1987 | Higuchi ..................... | 310/90.5 |
| 4,688,998 A | 8/1987 | Olsen et al. ................. | 417/356 |
| 4,769,031 A | 9/1988 | McGough et al. ............. | 623/1 |
| 4,863,461 A | 9/1989 | Jarvik ........................... | 623/3 |
| 4,880,352 A * | 11/1989 | Aarestad .................. | 415/182.1 |
| 5,044,897 A | 9/1991 | Dorman .................... | 417/423.7 |
| 5,055,005 A | 10/1991 | Kletschka .................... | 417/356 |
| 5,112,202 A | 5/1992 | Oshima et al. ............. | 417/423 |
| 5,195,877 A | 3/1993 | Kletschka .................... | 417/356 |
| 5,302,874 A | 4/1994 | Pinkerton .................. | 310/90.5 |
| 5,326,344 A | 7/1994 | Bramm et al. ................. | 623/3 |
| 5,385,581 A | 1/1995 | Bramm et al. ................. | 623/3 |
| 5,470,208 A | 11/1995 | Kletschika .................. | 417/356 |
| 5,576,587 A | 11/1996 | Takahashi et al. ......... | 310/90.5 |
| 5,666,014 A | 9/1997 | Chen .......................... | 310/90.5 |
| 5,685,700 A | 11/1997 | Izraelev .................... | 417/423.7 |
| 5,722,429 A | 3/1998 | Larson, Jr. et al. ......... | 128/899 |
| 5,728,069 A * | 3/1998 | Montevecchi et al. ...... | 604/151 |
| 5,777,414 A | 7/1998 | Conrad ...................... | 310/90.5 |
| 5,783,885 A | 7/1998 | Post ........................... | 310/90.5 |
| 5,840,070 A | 11/1998 | Wampler .................... | 604/131 |

(Continued)

FOREIGN PATENT DOCUMENTS

JP 2-17061 * 1/1990

(Continued)

*Primary Examiner*—Alvin J. Stewart
*Assistant Examiner*—Javier G. Blanco
(74) *Attorney, Agent, or Firm*—Metcalf Intellectual Property Law, LLC

(57) ABSTRACT

A low profile pump inlet for an implantable blood pump is disclosed. The low profile pump inlet has an inflow diffuser for attachment to a conduit bearing an inflow of a fluid such as blood and an outflow orifice in fluid connection with the diffuser. The outflow orifice is configured to direct the fluid from the diffuser into a pump such as an implantable blood pump. The low profile pump inlet helps to suppress the effects of upstream pipe bends on the blood traveling through the inlet. The inlet thus provides a flow having a substantially uniform velocity profile into the blood pump.

48 Claims, 3 Drawing Sheets

U.S. PATENT DOCUMENTS

| | | |
|---|---|---|
| 5,911,558 A | 6/1999 | Nakazeki et al. ............ 415/118 |
| 5,928,131 A | 7/1999 | Prem ............................ 600/16 |
| 5,938,412 A | 8/1999 | Izraelev ................... 417/423.7 |
| 5,968,053 A | 10/1999 | Revelas ...................... 606/108 |
| 5,980,448 A | 11/1999 | Heilman et al. |
| 6,001,056 A | 12/1999 | Jassawalla et al. ............ 600/16 |
| 6,015,275 A | 1/2000 | Suzuki et al. .......... 417/423.12 |
| 6,074,180 A | 6/2000 | Khanwilkar et al. ........ 417/356 |
| 6,080,133 A | 6/2000 | Wampler ...................... 60/131 |
| 6,129,660 A | 10/2000 | Nakazeki et al. ............. 600/17 |
| 6,146,325 A | 11/2000 | Lewis et al. ................... 600/16 |
| 6,244,835 B1 | 6/2001 | Antaki et al. ................ 417/356 |
| 6,293,901 B1 | 9/2001 | Prem ............................ 600/17 |
| 6,302,661 B1 | 10/2001 | Khanwilkar et al. |
| 6,375,607 B1 | 4/2002 | Prem ............................ 600/17 |
| 6,394,769 B1 | 5/2002 | Bearnson et al. ......... 417/423.7 |
| 2002/0045846 A1 | 4/2002 | Kaplon et al. .................. 604/9 |

FOREIGN PATENT DOCUMENTS

| WO | WO 99/53974 | 10/1999 |
|---|---|---|

\* cited by examiner

LOW PROFILE INLET FOR AN IMPLANTABLE BLOOD PUMP

BACKGROUND OF THE INVENTION

1. Field of the Invention

The present invention relates to pumps for pumping fluids such as blood that are sensitive to mechanical forces or shear stress. More particularly, the present invention is a low profile pump inlet for use with a blood pump which may be implanted into a patient.

2. Description of Related Art

Many pumps are known in the art for pumping fluids in a wide range of applications. The basic function of such pumps is to either move a fluid from one point to another, or to impart energy to the fluid, raising it from one energy level to another. Recently, pumps have begun to be developed for use with sensitive fluids such as blood. Such pumps present very specific design requirements in order to function properly. Specifically, if a blood pump is intended to be used to support or assist the blood flow of a human patient, it must operate to move and raise the energy level of a blood flow without causing undue damage to the blood. Further, such pumps must operate without giving rise to illness in the patient. This is true whether the pump is intended for external use or for implantation.

Much research is currently in progress to develop implantable blood pumps such as ventricular assist devices (or "VADs") and heart-replacement devices for use in a human patient for both short- and long-term use. When such pumps are intended for use in human patients, they face unique design challenges, including size and shape restraints, durability requirements, specific blood flow characteristics, and energy consumption restraints. These design challenges often dictate the usability of a potential pump in that they determine whether or not the pump will function sufficiently to sustain life without causing injury to the patient.

It is desirable to limit the size of an implantable pump in order to assure that it may be implanted in a patient without causing undue impingement on the patient's organs. Further, the implanted pump must be safely supported inside the patient, thus further restricting the size of the pump. Additionally, it is desirable to use a pump assembly that is durable, and which may last for a period of years. Yet further, an implantable blood pump needs to provide an even outflow of blood with a substantially smooth flow pattern in order to avoid stagnation or recirculation within the pump. Such improper flows diminish the efficiency of the pump, and may cause thrombosis or hemolysis, which could cause injury to a patient. Finally, a pump should be efficient in its energy consumption in order to prolong its periods of operability without requiring user intervention.

Many of these design considerations are influenced by the inlet used to carry the blood to be pumped into an internal chamber of the implantable pump. Such inlets may be relatively large in size, thus occupying a large volume, and contributing significantly to the weight of the complete pump apparatus. In addition, the inlets may simply carry a fluid without acting on the flow patterns of the blood passing through them. Turbulent flow patterns may exist in a blood flow due to bends and turns in the inflow conduit used to supply blood to the pump. Such curves may be required for proper installation and placement of the device in a specific patient. These design constraints could result in an uneven distribution of blood into the pump or thrombus formation. These conditions may cause inefficiency in the operation of the pump, or danger to the patient. Such inefficiency may affect the fluid circulating performance of the pump as well as the energy consumption characteristics of the pump.

Accordingly, it would be an advantage to provide a pump inlet for use with an implantable blood pump that had a low profile. It would be a further improvement to provide a pump inlet that at least partially suppresses undesirable flow patterns resulting from upstream bends and turns in a flow path, thus providing a substantially smooth outflow into the pump having a relatively uniform velocity profile. It would also be an improvement in the art to provide a pump inlet that distributes an outflow of blood substantially evenly about the impeller of a pump to promote the efficient operation of the implantable blood pump.

Such an apparatus is disclosed herein.

SUMMARY OF THE INVENTION

The apparatus of the present invention has been developed in response to the present state of the art, and in particular, in response to the problems and needs in the art that have not yet been fully solved by currently available pump inlets for implantable blood pumps. Thus, the present invention provides a low profile pump inlet for use with implantable blood pumps.

The apparatus of the invention is thus a low profile inlet for use with an implantable blood pump. The low profile inlet includes an inflow diffuser and an outflow orifice for directing a flow of a fluid inward from an inflow conduit, altering its flow path, and directing it into an implantable blood pump. The inflow diffuser spreads and divides the flow of fluid in order suppress turbulent flow patterns imparted to the flow upstream. The diffuser also supplies the flow substantially evenly about an outflow orifice which directs the flow into a pump. The outflow orifice receives a flow of fluid from the diffuser. The outflow orifice then gradually changes the flow direction of the fluid to direct it into an implantable blood pump with a substantially uniform velocity profile.

In a preferred embodiment of the invention, the diffuser includes a tapered region leading to the outflow orifice and two intersecting arcuate channels in continuous fluid communication with the outflow orifice. In some embodiments of the invention, the arcuate channels may be symmetrical. This may provide a fluid outflow that is substantially without vortex flow as it enters the pump. In other embodiments of the invention, the arcuate channels may be asymmetrical to provide a fluid outflow that exhibits a predetermined vortex flow as it enters the pump. Such a vortex flow may be desired for use with specific pump designs.

In the low profile pump inlet, the intersecting arcuate channels are used to distribute the fluid about the outflow orifice. As such, the channels serve to define a flow path for the fluid about the orifice. In a preferred embodiment of the invention, the arcuate channels define at least a substantially cardioid flow path. Such a path allows for the flow of fluid to be distributed evenly about the outflow orifice. Additionally, the arcuate path aids in substantially suppressing flow patterns caused by upstream bends or turns in an inflow conduit that would otherwise remain in the fluid flow.

Heart assist devices are generally implanted into a patient in a location that provides for safe operation of the device without impinging on internal organs or causing discomfort to the patient. Since patients vary in shape and size, flexibility in installation is imperative to allow optimal positioning of a device. In the case of a heart-assist device such as a ventricular assist device, flexibility in installation becomes a troublesome issue since the introduction of bends into fluid conduits to accommodate a specific patient may generate recirculating flow, stagnation, or other fluid flow patterns that decrease the efficiency of the pump.

The low profile pump inlet of the invention may be configured to remove such flow patterns, thus enhancing the performance of the pump. Specifically, the velocity profile of the outflowing fluid is made substantially uniform. This improves the efficiency of the pump. Additionally, by controlling and standardizing the flow, it may be better controlled. Specifically, the pump inlet serves to substantially eliminate recirculating flow and stagnation, thus eliminating causes of thrombosis and potential clotting in the device itself. The pump inlet of the invention thus allows a surgeon installing an implantable blood pump to bend and direct the fluid conduits associated with the pump without affecting the performance of the pump.

The pump inlet also includes an outflow orifice that receives fluid channeled to it by the inflow diffuser and directs it into the pump. In a preferred embodiment of the invention, the outflow orifice is annular in shape and has an outer wall which curves inwardly from the interface of the outflow orifice with the arcuate channels. The outflow orifice is configured to direct the fluid from the diffuser into the pump at an angle from the flow path the fluid traveled as it entered the inlet. In a preferred embodiment of the invention, the outflow orifice is configured to direct the fluid into the pump at an angle substantially perpendicular to the flow path of the fluid as it entered the inlet. The outflow orifice may alternatively have a tubular configuration.

In another embodiment, the invention is an implantable blood pump including a low profile pump inlet. Such a blood pump includes components such as a pump housing, a low profile pump inlet, an impeller, and a pump outlet. The low profile pump inlet of the implantable blood pump generally includes an inflow diffuser and an outflow orifice similar to those described above.

In contrast to the standalone pump inlet described above, in this embodiment, the low profile pump inlet may be constructed as an integral part of the pump housing. Specifically, components of the pump inlet such as the inflow diffuser and the outflow orifice may be in whole, or in part built into the housing of the implantable blood pump.

These and other features and advantages of the invention will become more fully apparent from the following description and appended claims. They will also be learned by the practice of the invention as set forth hereinafter.

BRIEF DESCRIPTION OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the apparatus of the present invention, as represented in FIGS. 1 through 6, is not intended to limit the scope of the invention, as claimed, but is merely representative of presently preferred embodiments of the invention.

Figure 1:
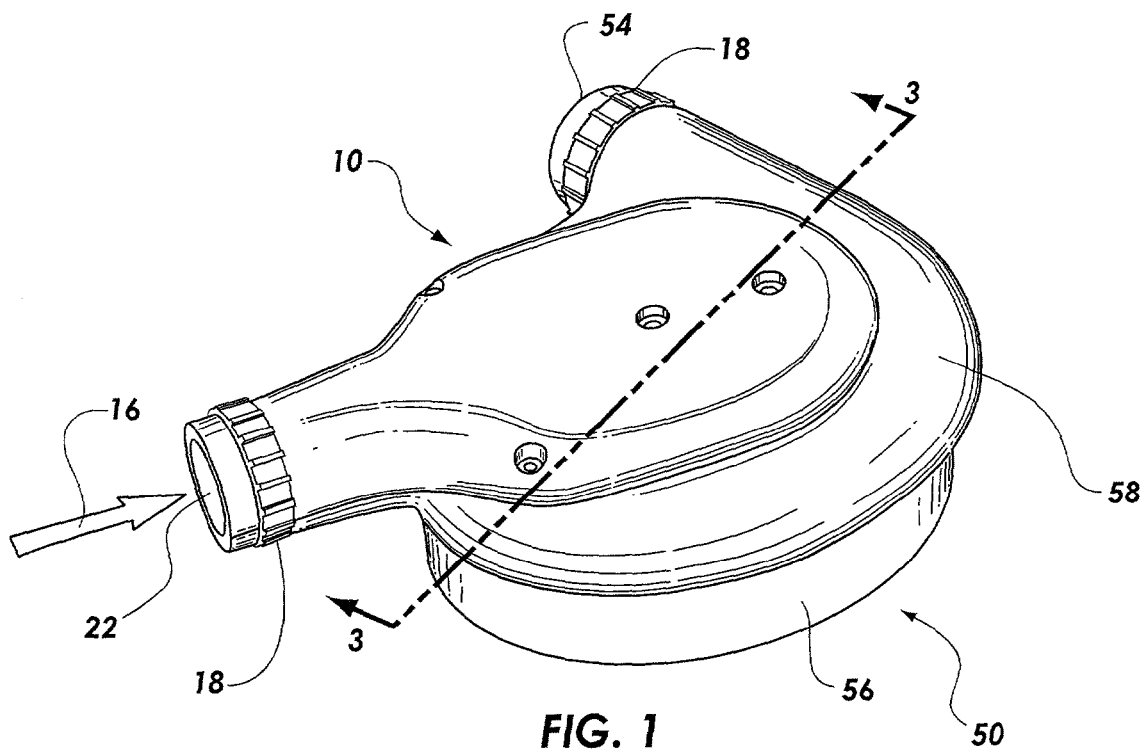
FIG. 1 is a perspective view of a low profile pump inlet of the invention attached to an implantable blood pump.

Referring now to FIG. 1, an implantable blood pump including a low profile pump inlet according to the invention is shown in perspective. Specifically, a pump inlet 10 is shown attached to an implantable blood pump 50. In this Figure, the pump inlet 10 is shown to include an inlet 22 and a coupling 18. The inlet 22 accepts an inflow of a fluid 16, such as blood, into the pump inlet 10. The coupling 18 allows the pump inlet 10 to be attached to an inflow conduit or other tube (not shown) in a sealed and secure manner to prevent leakage of the fluid 16 and detachment of the conduit from the pump inlet 10.

The pump 50 is generally configured to receive a flow of blood 16 through an inlet 10. The inlet 10 transmits the flow of blood 16 into the pump itself inside the pump housing 56. The pump 50 then imparts energy to the flow of blood 16, pushing it into the pump volute 58, through which it travels to the pump outlet 54. The flow of blood 16 is then transmitted back into the circulatory system of the patient. In some instances, the pump 50 receives the flow of blood 16 from the patient's heart and returns it to the circulatory system. In some specific instances, the pump may receive the flow of blood 16 from the left ventricle of a patient and return it to the patient's aorta, forming an aortic anastomosis.

The low profile pump inlet 10 of the invention is used with an implantable blood pump 50 to receive a flow of blood 16 and route it into the pump 50. The low profile pump inlet 10 of the invention acts to remove undesirable flow patterns within the flow of blood 16 caused by upstream bends in fluid conduits. This allows the even distribution of the flow of blood 16 into the pump at a substantially uniform velocity profile. The low profile inlet 10 of the invention also prevents recirculating and stagnant flow, thus improving the overall performance of the pump 50. The low profile inlet 10 of the invention may be a separate piece attached to the pump 50, or may be integrally molded, in whole or in part, into the housing 56 of the pump 50.

Figure 2:
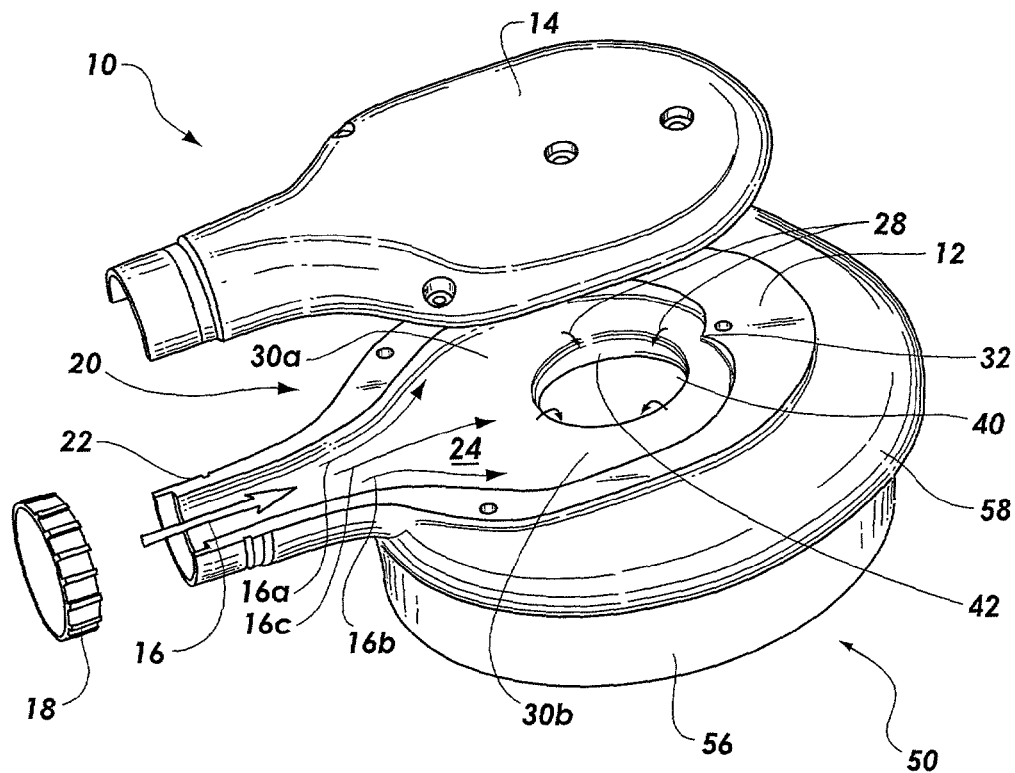
FIG. 2 is an exploded perspective view of the low profile pump inlet of FIG. 1.

Referring now to FIG. 2, an exploded perspective view of the implantable blood pump 50 having a low profile pump inlet 10 of FIG. 1 is shown. In this embodiment, the pump inlet 10 has an inlet base 12 and an inlet cap 14. FIG. 2 shows the inlet base 12 and the inlet cap 14 separated to illustrate the features of the interior of the inlet 10.

The pump inlet 10 includes an inflow diffuser 20 and an outflow orifice 40. The inflow diffuser 20 diffuses, divides, and channels a flow of fluid 16 received from the body evenly about the outflow orifice 40, which guides the fluid 16 into the pump. The inflow diffuser 20 of the pump inlet 10 includes an inlet 22, a tapered region 24, and arcuate channels 30a, 30b. The outflow orifice 40 may include an outer wall 42 and an inner wall 44. The components of the pump inlet 10 are in fluid communication with each other.

The inlet 22 of the inflow diffuser 20 is a generally tubular component that may be attached to a conduit or other device providing an inflow of a fluid 16 such as blood to the pump 50. The inlet 22 attaches to the conduit in a sealed, secure manner to receive this flow of fluid 16, and may be composed of a tubular region defined by a portion of the inlet cap 14 and the inlet base 12. The inlet 22 of the inflow diffuser 20 then directs the flow of fluid 16 into the tapered region 24 and the arcuate channels 30a, 30b.

The tapered region 24 of the inlet 20 is a transitional region in which the tubular inlet 22 is gradually flattened to better conform to the flat profile of the pump inlet 10. This flattening helps to suppress undesirable flow patterns taken on by the fluid in upstream features such as bends in fluid conduits. In addition, the tapered region 24 widens, creating a broader, flattened pathway for the fluid 16 and further suppressing undesirable flow patterns. The uneven or undesirable flow patterns may have been caused by bends or curves encountered in upstream fluid conduits (not shown). The overall ability of the pump inlet to remove such undesirable flow patterns affords flexibility to the medical professional surgically installing the implantable blood pump 50 of the invention. Specifically, by providing a diffuser 20 capable of rendering a fluid flow that is substantially uniform, the medical professional may place the pump 50 in a variety of positions in the body of the patient, including positions having curved or bent inflow conduits, without diminishing the performance of the pump 50. This allows the installer to use the device in patients whose anatomy requires the pump to be placed at an angle to or rotated from positions not requiring bends and curves in the conduits attaching the pump 50 to the heart.

The tapered region 24 is created as either or both of the inlet base 12 and the inlet cap 14 impinge into the interior of the inlet 22 to narrow the flow path available to the fluid 16 leading to the outflow orifice 40. Fluid 16c directed through the center of the tapered region 24 is channeled directly into the outflow orifice 40. Flows 16a, 16b directed nearer to the ends of the tapered region 24 are directed into the arcuate channels 30a, 30b.

The arcuate channels 30a, 30b each travel outwardly from the inlet 22 and then reunite at a cusp 32 to define a substantially cardioid pathway. These channels 30a, 30b act to spread and to partially divide the flow of fluid 16 by distributing it around the periphery of the outflow orifice 40.

In presently preferred embodiments of the invention, the arcuate channels 30a, 30b are symmetrical. This provides an even distribution of the fluid 16 around the outflow orifice 40. In some embodiments, this property is desirable because it renders the velocity profile of the fluid outflow 28 exiting the pump 50 substantially uniform.

In practice, it is desirable to control the velocity and flow characteristics of the fluid outflow 28 exiting the inlet 10 into the pump 50. In many implantable blood pumps, the pump such as 50 is a rotary pump. In many cases, the efficiency of such a pump is enhanced by supplying it with a constant flow of blood 28 that is uniform in its flow pattern and in its velocity. In some cases, the impeller of the pump may function more efficiently when the outflow of blood 28 is distributed evenly about a central axis of the pump impeller while having a substantially uniform velocity and flow patterns.

In alternate embodiments, the arcuate channels 30a, 30b may be made asymmetrical. In such embodiments, one arcuate channel such as, for example, 30a may be made longer than the arcuate channel 30b. In this configuration, the arcuate channels 30a, 30b will meet in a location not along a midline of the pump inlet 10. Such a configuration may result in the outflow 28 having a net residual of angular momentum. This imparts a vortex flow to the outflow 28 as it exits the pump inlet 10 through the outflow orifice 40. Such a vortex flow may be desirable for use with specific pump configurations, including pumps with impellers adapted to receive a vortex flow of fluid. Asymmetry may similarly be imparted to the arcuate channels 30a, 30b by making one of the channels slightly larger or smaller than the other. This allows the amounts of fluid flowing through the channels 30a, 30b to be equal, similarly resulting in residual angular momentum. In addition, a fluid outflow exhibiting vortex flow may be provided by eliminating one of the arcuate channels entirely and instead extending the remaining arcuate channel to travel completely about the outflow orifice 40.

With continuing reference to FIG. 2, the pump inlet 10 acts on a fluid flow 16. The fluid flow 16 enters the inlet 22 of the pump inlet 10. The flow 16 travels along inlet 22, after which it encounters an inflow diffuser 20. The inflow diffuser 20 suppresses undesirable flow patterns found in the flow of fluid 16 by broadening the cross-sectional area of the flow path and by flattening the round profile of the flow path. As the diffuser 20 suppresses undesirable flow patterns, it directs the flow 16 toward an outflow orifice 40, which in this embodiment has an annular shape.

The inflow diffuser 20 also partially divides the flow of fluid 16 into flows 16a and 16b which travel substantially along arcuate channels 30a, 30b; and into flow 16c which travels substantially directly through the inflow diffuser 20 into the outflow orifice 40.

Flows 16a, 16b, and 16c are spread out along the circumference of the outflow ring 40 by the diffuser 20 and the arcuate channels 30a, 30b. The arcuate channels 30a, 30b culminate at a cusp 32, where the channels 30a, 30b are united and directed into the outflow orifice 40. The channels 30a, 30b define a substantially cardioid flow path for the fluid 16. After the cusp 32, the flows 16a, 16b, and 16c are reunited as they are directed into the outflow orifice 40. The fluid 16 is distributed substantially evenly about the circumference of the outflow orifice 40 by flows 16a, 16b, and 16c. This results in a relatively even distribution of the fluid 16 as it is directed into the pump 50 and contacts the impeller (not shown). In combination, this provides an outflow 28 issuing from the outflow orifice 40 that has a substantially uniform velocity profile.

In the alternative embodiments mentioned above in which the arcuate channels 30a, 30b are asymmetrical either due to length or volume, or in which one of the arcuate channels is eliminated, the outflow 28 may have residual angular momentum, thus resulting in an outflow 28 exhibiting vortex flow.

Figure 3:
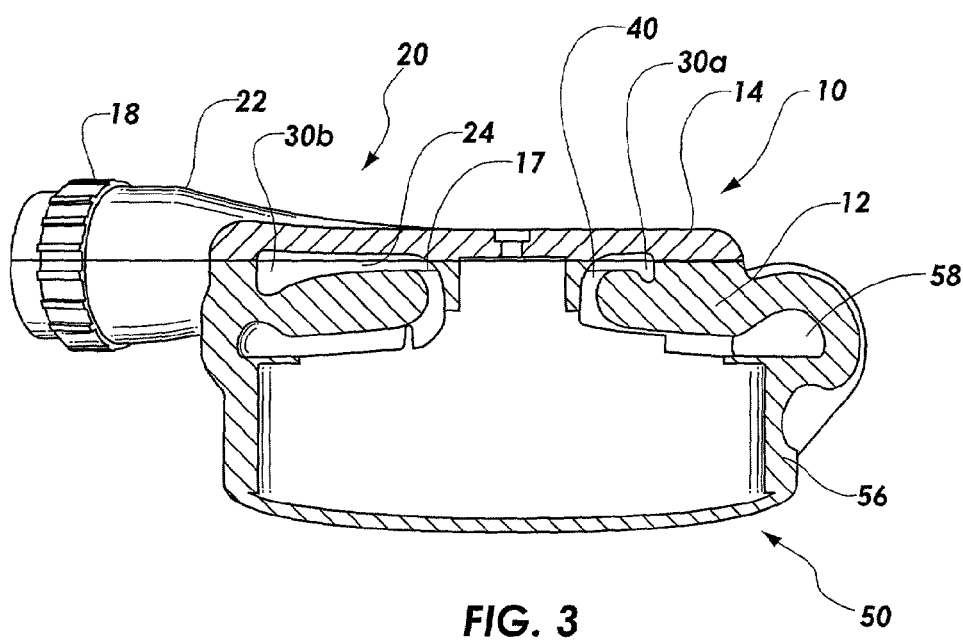
FIG. 3 is a cross sectional view of the low profile pump inlet of FIG. 1 taken from line 3-3 of FIG. 1.

Referring now to FIG. 3, a cross sectional view of the low profile pump inlet 10 and pump 50 of FIG. 1 taken at line 3-3 of FIG. 1 is shown. This figure shows a cross sectional view of the arcuate channels 30a, 30b and their relationship to the diffuser 20 and the outflow orifice 40. As is shown, the arcuate channels 30a, 30b begin in the tapered region 24 and continue in a substantially cardioid path, uniting at a cusp 32. In alternate embodiments, the arcuate channels 30a, 30b have a shape selected from the group of oval and circular, as well as similar irregular rounded shapes.

The arcuate channels 30a, 30b gradually taper inwardly, directing flows 16a, 16b, and 16c into the outflow orifice 40. The outflow orifice 40 in this embodiment is generally a circular, ring-shaped opening that directs a flow of fluid 16 from the pump inlet 10 into a pump 50. As noted above, however, the outflow orifice 40 may have other geometries, including tubular. As is seen in FIG. 3, the outflow orifice 40 may have curving walls to direct a flow of fluid 16 downwardly, changing the angle of its flow. In some embodiments, the orifice 40 changes the angle of the flow 16 about 90 degrees to produce an outflow 28 perpendicular to the inflow 16. In other embodiments, it may be desirable to change the angle of the flow to produce an outflow having an angle greater or less than 90 degrees, producing a non-perpendicular outflow 28.

Figure 4:
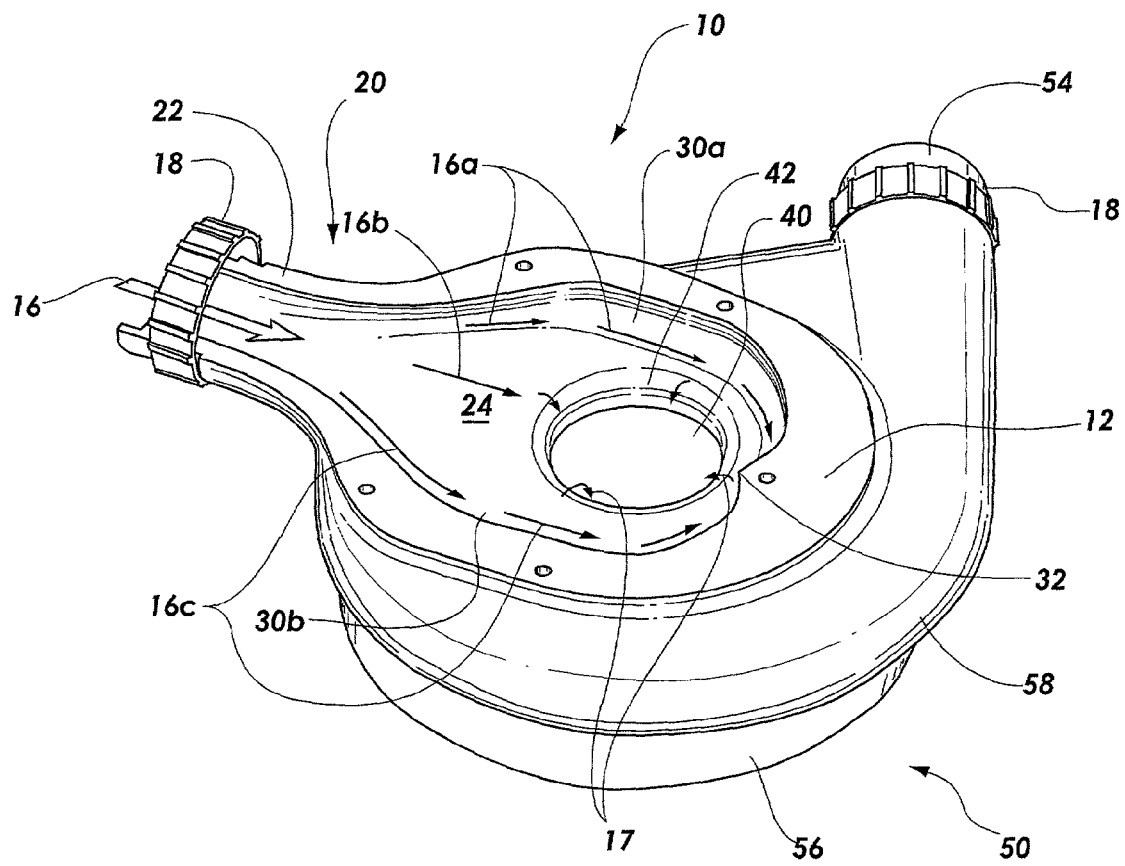
FIG. 4 is a perspective view of the low profile pump inlet of FIG. 1 shown with the inlet cap removed.

Referring now to FIG. 4, an isolated perspective view of the inlet base 12 of the pump inlet 10 is shown attached to pump 50. In this figure, the inlet base 12 is shown to largely define the arcuate channels 30a, 30b. In some embodiments, this provides a pump inlet 10 carrying most of its internal volume below the midline of the pump inlet 10. As is visible in FIG. 4, the arcuate channels 30a, 30b allow the pump inlet 10 to turn the flow 16 up to 180 degrees to provide a substantially even outflow 28 to the pump 50.

Further, the outflow orifice 40 and arcuate channels 30a, 30b allow the outflow 28 to have a substantially uniform exit velocity distribution/velocity profile. This improves the efficiency of the pump 50 as a whole, as well as the flow pattern of the fluid within the pump and as it exits the pump through the outlet 54.

As is seen in FIG. 4, the inlet base 12 also helps to define the outflow orifice 40. Specifically, the inlet base 12 defines an outer wall 42 of the outflow orifice 40. The outer wall 42 pairs with the inner wall 44 to form a curving outflow orifice 40. The flow is often turned to initially be at least perpendicular to the inflow 16.

Figure 5:
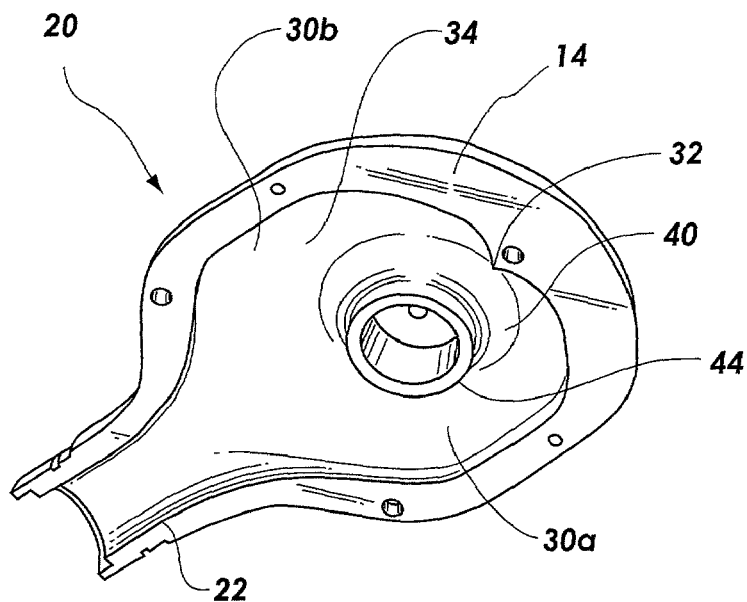
FIG. 5 is a perspective view of the inlet cap of the low profile pump inlet of FIG. 1.

FIG. 5 is an isolated perspective view of the inlet cap 14 of the pump inlet 10 shown in FIG. 1. As is visible in FIGS. 2 and 5, the cap may be substantially flat on its outer surface. The edges of the cap 14 are generally rounded and, in this embodiment, the inlet cap 14 is substantially oval-shaped. In alternative embodiments, the inlet cap 14 may be shaped differently. In one example, the inlet cap 14 may be shaped in at least a partially cardioid manner. This may allow it to be conformed to the shape of the arcuate channels 30a, 30b in order to save weight and material. The inlet cap 14 is generally attached to the inlet base 12 in a secure and sealed manner to assure its proper positioning and prevent leakage of the fluid flowing through the inlet 22.

The cap 14 cooperates with the inlet base 12 to define the inlet 22, inflow diffuser 20, and outflow orifice 40. In this embodiment, the inlet cap 14 may include a part of the inlet 22, such as a half-tubular portion which unites with a half-tubular portion on the inlet base 12 to form the inlet 22.

Additionally, the cap 14 may help to define the inflow diffuser 20. This is seen in FIG. 5 as the inlet cap 14 includes a tapered region 24 which, when the cap is attached to the inlet base 12, forms a portion of the tapered region. The cap 14 similarly helps to define the arcuate channels 30a, 30b. As shown in the embodiment of FIG. 5, the top inside of the cap defines a ceiling 34 for the channels 30a, 30b, which acts to guide the fluid flowing through the channels 30a, 30b to the outflow orifice 40. It additionally may include a portion of the cusp 32 of the inlet base 12.

Finally, in this embodiment, the inlet cap 14 helps to define the annular outflow orifice 40. Specifically, in embodiments of the pump inlet having an annular outflow orifice, the inlet cap 14 may include an inner wall 44 of the outflow orifice 40. This inner wall 44 pairs with the outer wall 42 of the inlet base 12 to form the annular outflow orifice 40. In embodiments having alternatively-shaped outflow orifices, the inlet cap 14 may be configured to cooperate with the base to define the shape of the outflow orifice.

Figure 6:
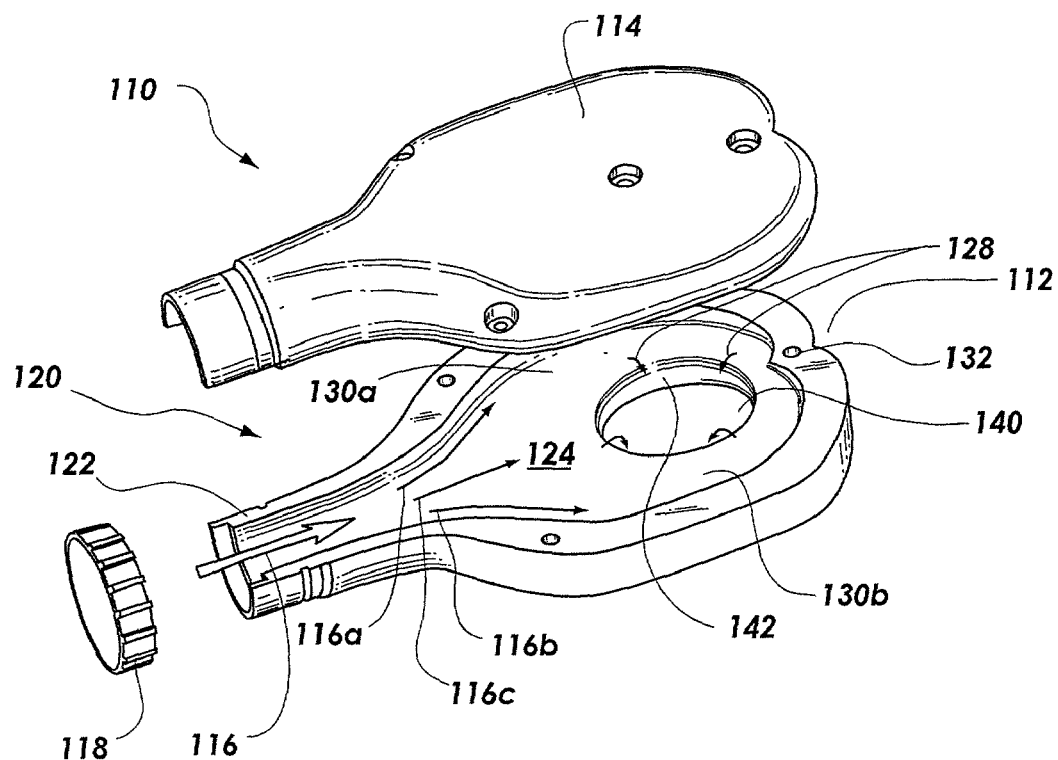
FIG. 6 is an exploded perspective view of an alternate embodiment of a low profile pump inlet.

FIG. 6 is an exploded perspective view of a low profile pump inlet 110. In this embodiment of the pump inlet of the invention, the pump inlet 110 has an inlet base 112 and an inlet cap 114. In FIG. 6, the inlet base 112 and the inlet cap 114 are separated to illustrate the features of the interior of the inlet 110. This pump inlet 110 is configured to be constructed separately from the housing of an implantable blood pump and then attached to such a pump.

Although such a separate pump inlet 110 may use other suitable outer shapes, including the shape of the embodiment of FIGS. 1-5, the outer shape of the pump inlet 110 may be constructed to mirror the cardioid shape of the arcuate channels 130a, 130b of the inlet 110 as is shown. Such a configuration may allow the inlet 110 to be constructed using less material, thus possibly resulting in a lighter inlet 110 and possibly reducing the cost of the inlet 110.

As in the other embodiments shown in previous figures, the pump inlet 110 includes an inflow diffuser 120 and an outflow orifice 140. The inflow diffuser 120 diffuses, divides, and channels a flow of fluid 116 received from the patient about the outflow orifice 140. The outflow orifice 140 is configured to be attached to a pump (not shown) and to guide the fluid 116 into the pump.

As noted above, the outflow orifice 140 may have a variety of geometries, including tubular and annular. Outflow orifice 140 of FIG. 6 is tubular, and thus includes only an outer wall 142 constructed into the inlet base 112. The inlet cap 114 generally includes no inner wall such as 44 of FIG. 5, but may, however, be constructed to include surface features to aid fluid flow into the outlet orifice 140.

The inlet 122 of the inflow diffuser 120 of the pump inlet 110 is a generally tubular component formed by the joined inlet cap 114 and inlet base 112. The inlet cap 114 and inlet base 112 attach to each other in a sealed manner to prevent escape of the fluid 116 channeled through the inlet 110. Further the inlet 122 of the inflow diffuser 120 may be attached to a conduit or other device providing the inflow of blood 116 to a pump attached to the inlet 110.

The inlet 122 of the inflow diffuser 120 is configured to direct the flow of fluid 116 into a tapered region 124 of the inflow diffuser 120 and into the arcuate channels 130a, 130b. The tapered region 124 of the inlet 120 is a transitional region. It is here that the inlet 122 is flattened to better conform to the flat profile of the pump inlet 110 and to suppress undesired flow patterns present in the flow of fluid 116. The tapered region 124 may be defined by the inlet base 112 and/or the inlet cap 114. In the tapered region 124, the flow path of the fluid 116 is flattened and widened. As a result, the flow of fluid is split. Flow 116c is partially directed toward the outflow orifice 140, while flows 116a and 116b are directed to the ends of the tapered region 124 and into the arcuate channels 130a, 130b for distribution to the outflow orifice 140.

The arcuate channels 130a, 130b each travel outwardly from the inlet 122 and reunite at a cusp 132 to define a substantially cardioid pathway. As above, this pathway may be symmetrical or asymmetrical. Alternatively, the pathway may be defined by a single arcuate channel to provide an asymmetrical pathway. As noted, asymmetrical flow pathways may produce an outflow 128 exhibiting vortex flow. The channels 130a, 130b spread and divide the flow of fluid 116 by distributing it around the periphery of the outflow orifice 140.

Thus, the invention provides a low profile pump inlet for use with an implantable blood pump. The inlet is often composed of an inlet cap and an inlet base which cooperate to provide an inlet with a sealed flow path for directing the fluid into a pump. The low profile pump inlet includes a flow diffuser configured to be attached to a fluid conduit. The flow diffuser acts to suppress undesirable flow patterns by broadening the cross-sectional diameter of the flow path provided for a fluid entering the inlet. Further, the flow diffuser flattens the profile of this flow path, thus additionally suppressing undesirable flows.

The flow diffuser of the low profile pump inlet includes at least one arcuate channel for directing the flow of fluid about an outflow orifice present in the base of the pump inlet. The flow diffuser preferably includes two substantially symmetrical arcuate channels that meet at a cusp. These channels define a substantially cardioid flow pathway for the fluid. These components allow the low profile pump inlet of the invention to provide an evenly-distributed outflow into the pump having a substantially uniform velocity profile.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed and desired to be secured by United States Letters Patent is:

1. A low profile pump inlet comprising an inflow diffuser and an outflow orifice, wherein the diffuser is defined by an open, unobstructed chamber having two intersecting arcuate channels in direct, continuous fluid connection with the outflow orifice about an inner periphery of the intersecting arcuate channels, wherein the outflow orifice is configured to direct a fluid from the diffuser into a pump, and wherein the arcuate channels define a substantially cardioid flow path.

2. The low profile pump inlet of claim 1, wherein the arcuate channels are symmetrical.

3. The low profile pump inlet of claim 1, wherein the outflow orifice curves inwardly from the arcuate channels.

4. The low profile pump inlet of claim 1, wherein the outflow orifice is configured to direct the fluid from the diffuser into the pump at an angle from the original flow path of the fluid.

5. The low profile pump inlet of claim 1, wherein the outflow orifice is configured to direct the fluid into the pump at an angle substantially perpendicular to the original flow path of the fluid.

6. The low profile pump inlet of claim 1, wherein the outflow orifice is annular in shape.

7. The low profile pump inlet of claim 1, wherein the outflow orifice directs the fluid into the pump with a substantially uniform velocity.

8. The low profile pump inlet of claim 1, wherein the outflow orifice directs the fluid into the pump with a substantially uniform velocity independent of any flow patterns upstream of the pump inlet.

9. The low profile pump inlet of claim 1, wherein the inflow diffuser of the pump inlet is configured to direct the fluid into the outflow orifice such that the fluid enters the pump without vortex flow.

10. The low profile pump inlet of claim 1, wherein the inflow diffuser further comprises a tapered region for suppressing undesirable flow patterns in the fluid.

11. The low profile pump inlet of claim 10, wherein the tapered region is flattened.

12. The low profile pump inlet of claim 10, wherein the tapered region broadens the cross-sectional area of the inflow diffuser.

13. The low profile pump inlet of claim 10, wherein the tapered region is flattened and broadens the cross-sectional area of the inflow diffuser.

14. A low profile pump inlet for a blood pump, the inlet comprising an inlet base and an inlet cap such that when the base and the cap are joined together they jointly form an inflow diffuser, the diffuser being defined by an open, unobstructed chamber having two intersecting arcuate channels defining a substantially cardioid flow path, and an outflow orifice, wherein the arcuate channels are in substantially continuous fluid connection with the outflow orifice about an inner periphery of the intersecting arcuate channels, and wherein the outflow orifice is configured to direct the fluid from the diffuser into the blood pump.

15. The low profile pump inlet of claim 14, wherein the arcuate channels are symmetrical.

16. The low profile pump inlet of claim 14, wherein the outflow orifice curves inwardly from the arcuate channels.

17. The low profile pump inlet of claim 16, wherein the outflow orifice is configured to direct the fluid from the diffuser into the pump at an angle from the original flow path of the fluid.

18. The low profile pump inlet of claim 17, wherein the outflow orifice is configured to direct the fluid into the pump at an angle substantially perpendicular to the original flow path of the fluid.

19. The low profile pump inlet of claim 14, wherein the outflow orifice is annular in shape.

20. The low profile pump inlet of claim 14, wherein the outflow orifice directs the fluid into the pump with a substantially uniform velocity.

21. The low profile pump inlet of claim 20, wherein the outflow orifice directs the fluid into the pump with a substantially uniform velocity independent of any flow patterns upstream of the pump inlet.

22. The low profile pump inlet of claim 14, wherein the inflow diffuser of the pump inlet is configured to direct the fluid into the outflow orifice such that the fluid enters the pump without vortex flow.

23. The low profile pump inlet of claim 14, wherein the inflow diffuser further comprises a tapered region for suppressing undesirable flow patterns in the fluid.

24. The low profile pump inlet of claim 23, wherein the tapered region is flattened.

25. The low profile pump inlet of claim 23, wherein the tapered region broadens the cross-sectional area of the inflow diffuser.

26. The low profile pump inlet of claim 23, wherein the tapered region is flattened and broadens the cross-sectional area of the inflow diffuser.

27. A low profile pump inlet for directing a fluid into an implantable blood pump, the inlet comprising an inflow diffuser defined by an open, unobstructed chamber having two intersecting arcuate channels defining a substantially symmetrical cardioid flow path, and an outflow orifice, wherein the arcuate channels are in direct, continuous fluid connection with the outflow orifice about an inner periphery of the intersecting arcuate channels, and wherein the outflow orifice is configured to direct the fluid from the diffuser into the implantable blood pump at an angle substantially perpendicular to the original flow path of the fluid.

28. The low profile pump inlet of claim 27, wherein the outflow orifice is annular in shape.

29. The low profile pump inlet of claim 27, wherein the outflow orifice curves inwardly from the arcuate channels.

30. The low profile pump inlet of claim 27, wherein the outflow orifice directs the fluid into the implantable blood pump with a substantially uniform velocity.

31. The low profile pump inlet of claim 30, wherein the outflow orifice directs the fluid into the implantable blood pump with a substantially uniform velocity independent of any flow patterns upstream of the pump inlet.

32. The low profile pump inlet of claim 27, wherein the inflow diffuser of the pump inlet is configured to direct the fluid into the outflow orifice substantially without angular momentum such that the fluid enters the implantable blood pump without a vortex flow.

33. The low profile pump inlet of claim 27, wherein the inflow diffuser further comprises a tapered region for suppressing undesirable flow patterns in the fluid.

34. The low profile pump inlet of claim 33, wherein the tapered region is flattened.

35. The low profile pump inlet of claim 33, wherein the tapered region broadens the cross-sectional area of the inflow diffuser.

36. The low profile pump inlet of claim 33, wherein the tapered region is flattened and broadens the cross-sectional area of the inflow diffuser.

37. A low profile pump inlet for an implantable blood pump comprising:
an inflow tube;
an inflow diffuser attached to the inflow tube, the inflow diffuser comprising an inlet cap and an inlet base which together form a tube of gradually flattening and widening geometry;
wherein the diffuser is defined by an open, unobstructed chamber having a fluid flow path attached to the inflow diffuser; and
an outflow orifice; wherein the fluid flow path radiates from the inflow diffuser about the outflow orifice; and wherein the fluid flow path defines a substantially cardioid flow path.

38. The low profile pump inlet of claim 37, wherein the low profile pump inlet is composed of two halves which sealably join to cooperatively define the inflow tube, inflow diffuser, fluid flow path, and outflow orifice.

39. The low profile pump inlet of claim 37, wherein the fluid flow path is composed of two arcuate channels radiating from the inflow diffuser about the outflow orifice and uniting at a cusp.

40. The low profile pump inlet of claim 39, wherein the arcuate channels are symmetrical.

41. The low profile pump inlet of claim 37, wherein the outflow orifice is annular in shape.

42. A low profile pump inlet for directing a fluid, the pump inlet comprising:
a tubular inlet for receiving the fluid;
a tapered region in fluid connection with the tubular inlet;
a diffuser defined by an open, unobstructed chamber having a pair of intersecting arcuate channels extending from the tapered region and intersecting; and
an outflow orifice in direct, unobstructed, continuous fluid connection with the arcuate channels about an inner periphery of the intersecting arcuate channels; wherein the arcuate channels define a substantially cardioid flow path.

43. The low profile pump inlet of claim 42, wherein the tapered region is flattened to suppress undesirable flow patterns in the fluid.

44. The low profile pump inlet of claim 42 wherein the tapered region broadens the cross-sectional area of the tubular inlet.

45. The low profile pump inlet of claim 42, wherein the tapered region is flattened and broadens the cross-sectional area of the tubular inlet.

46. The low profile pump inlet of claim 42, wherein the arcuate channels are symmetrical.

47. The low profile pump inlet of claim 42, wherein the outflow orifice is configured to direct the fluid outwardly at an angle substantially perpendicular to the original flow path of the fluid.

48. The low profile pump inlet of claim 42, wherein the outflow orifice is annular in shape.

* * * * *